United States Patent [19]

Valyocsik et al.

[11] Patent Number: 4,923,690

[45] Date of Patent: May 8, 1990

[54] METHOD FOR PRODUCING HIGHLY SILICEOUS ZEOLITES

[75] Inventors: Ernest W. Valyocsik, Yardley, Pa.; Stephen S. Wong, Medord; Robert B. Calvert, Lawrenceville, both of N.J.

[73] Assignee: Mobil Oil Corporation, New York, N.Y.

[21] Appl. No.: 40,437

[22] Filed: Apr. 20, 1987

Related U.S. Application Data

[63] Continuation-in-part of Ser. No. 779,724, Sep. 24, 1985, abandoned, which is a continuation-in-part of Ser. No. 619,529, Jun. 11, 1984, abandoned.

[51] Int. Cl.$^5$ .............................................. C01B 33/28
[52] U.S. Cl. ..................................... 423/328; 423/329
[58] Field of Search ............... 423/329, 326, 328, 330; 502/60, 77

[56] References Cited

U.S. PATENT DOCUMENTS 3,308,069 3/1967 Wadlinger et al. ................. 423/328
4,570,027 2/1986 Boucher et al. .................... 585/467

OTHER PUBLICATIONS

Nature, 289 (1981), 782–783, von Ballmoos et al.

*Primary Examiner*—John Doll
*Assistant Examiner*—R. Bruce Breneman
*Attorney, Agent, or Firm*—Alexander J. McKillop; Charles J. Speciale; Malcolm D. Keen

[57] ABSTRACT

Large pore size zeolites produced with organic cations in the synthesis mixture are synthesized with high silica:alumina ratios by terminating the crystallization when the product is partly crystalline, preferably 30% to 90 % crystalline by X-ray diffraction measurement. The method is particularly useful with zeolite beta to produce a partly crystalline product with higher silica:alumina ratio by direct synthesis.

11 Claims, No Drawings

METHOD FOR PRODUCING HIGHLY SILICEOUS ZEOLITES

CROSS REFERENCE TO RELATED APPLICATION

This is a continuation-in-part of application Ser. No. 779,724, filed 24 Sept. 1985 which, in turn, was a continuation-in-part of Ser. No. 619,529, filed 11 June 1984 (both now abandoned).

FIELD OF THE INVENTION

This invention relates to a method for producing highly siliceous zeolites, especially zeolite beta.

More particularly, this invention relates to a method of preparing a highly siliceous, partially crystalline zeolite by a synthesis method of reduced cost. The products exhibit an extended, high silica/alumina mole ratio when compared to conventionally synthesized zeolites without the need for dealuminization. The zeolites prepared in this way show surprisingly high activity and selectivity in catalytic hydroisomerization processing.

BACKGROUND OF THE INVENTION

Crystalline zeolite beta and its conventional preparation are described in U.S. Pat. No. 3,308,069 and Re 28,341; the entire disclosure of each is incorporated in this specification by reference. It has a distinctive X-ray diffraction pattern which identifies it from other known crystalline silicates.

U.S. Pat. No. 4,284,529 claims a catalyst composition comprising an inorganic matrix and the alkali metal form of a steamed crystalline zeolite having a silica/alumina mole ratio above 12, a constraint index of from 1 to 12 and an alpha value of not less than 5, the catalyst composition having substantially no activity for cracking n-hexane. Zeolite beta prepared with tetraethylammonium ions as reaction mixture directing agent as in U.S. Pat. No. 3,308,069 is used as catalyst for hydrocracking $C_5+$ naphtha in U.S. Pat. No. 3,923,641.

A zeolite having the structure of zeolite beta is described in European Patent Application 55,046 (named "NU-2") and British Patent 2,024,790 (named "Boralite B"). Zeolite NU-2 is described in EU 55046 as being a member of the zeolite beta family of zeolites but with the distinction, among others, that it can only be prepared in pure form with products having a limited range of silica:alumina ratios, from 20:1 to 50:1. This distinctive character of NU-2 is affirmed by EU 187552. Zeolite beta, by contrast, may be prepared with silica:alumina ratios as high as 200:1 by the method disclosed by Wadlinger although higher values may be attained by dealuminisation, as described in U.S. Pat. No. 4,419,220.

When the proportion of silica in the zeolite is to be increased, resort may be made to dealuminisation methods but clearly, it would be desirable to produce zeolites directly with the desired silica:alumina ratio so as to avoid the subsequent dealuminisation step. However, the synthesis method may impose limits upon the silica:alumina ratio of the as-synthesised zeolite product. Zeolite beta, for example, is generally limited to a silica:alumina ratio of about 200:1.

Zeolites other than zeolite beta are shown prepared from various reaction mixtures having various silica/alumina reaction mixture mole ratios in U.S. Pat. Nos. 4,366,135; 4,297,335; 4,275,047 and 4,257,885. Preparation of zeolite ZSM-5 having a $SiO_2$ content of more than 90% by weight is described in European Patent Application 40,444. European Patent Application 36,683 and British Patent 1,553,209 disclose reaction mixture useful for preparing zeolites other than zeolite beta.

U.S. Pat. Nos. 4,088,605 and 4,148,713 disclose crystalline particles of ZSM-5 structure having an aluminum-free outer shell.

SUMMARY OF THE INVENTION

The present invention provides a method for preparing zeolite compositions exhibiting an extended range of product silica/alumina mole ratios. The method comprises forming a reaction mixture containing sources of alkali metal cations, organic nitrogen-containing cations, an oxide of aluminum, an oxide of silica and water and maintaining the mixture under crystallization conditions to produce a large pore size zeolite which has a crystallinity (by X-ray) of about 30% to 90% and of higher silica:alumina ratio than that possessed by the same zeolite when wholly (100%) crystalline. Generally, crystallization times will be from 24 hours to 7 days.

The method may be employed with large pore zeolites produced from synthesis mixtures containing organic nitrogen, for example, ZSM-20 and zeolite beta. The method is, however, of particular applicability with zeolite beta and is disclosed below with particular reference to zeolite beta for this reason. The other large pore zeolites capable of being produced from organic-containing synthesis mixtures may also be produced at higher product silica:alumina ratios by this method.

When the product zeolite is zeolite beta, the synthesis mixture contains sources of alkali metal cations, organic nitrogen-containing cations, an oxide of aluminum, an oxide of silicon and water and having a composition, in terms of mole ratios, within the following ranges:

|  | Broad | Preferred |
| --- | --- | --- |
| $SiO_2/Al_2O_3$ | 20–1000 | 30–500 |
| $H_2O/SiO_2$ | 5–200 | 10–100 |
| $OH^-/SiO_2$ | 0.10–2.0 | 0.2–1.0 |
| $M/SiO_2$ | 0.01–1.0 | 0.05–0.20 |
| $R/SiO_2$ | 0.10–2.0 | 0.20–1.0 |

R represents tetraethylammonium cations and M represents alkali metal cations. The mixture is maintained for from about 24 hours to about 7 days until the crystallinity (by X-ray) of the product zeolite Beta is from about 30% to about 90%. Crystallization is purposely terminated at a time which provides only from about 30% to about 90% crystallinity. Thereafter, the partially crystalline zeolite Beta is separated from the liquid and recovered.

Reaction conditions required consist of heating the foregoing reaction mixture to a temperature of from about 90° C. to about 200° C. for a period of time of from about 24 hours to about 7 days. A more preferred temperature range is from about 150° C. to about 160° C. with the amount of time at a temperature in such range being from about 48 hours to about 5 days.

The temperature/time relationship will be determined by the rate of crystallization, which must be terminated when the zeolite Beta is from about 30% to about 90% crystalline by X-ray analysis. Therefore, the digestion of the gel particles is carried out until zeolite Beta is formed having crystallinity from about 30% to about 90%. Crystallization is then terminated. The solid product is separated from the reaction medium, as by cooling the whole to room temperature, filtering and water washing.

When zeolite beta is the desired product, the key variables in the above reaction mixture composition are the molar ratios of $OH^-/SiO_2$ and $M/SiO_2$. If $OH^-/SiO_2$ is not optimized within the range of 0.10 to 2.0, and $M/SiO_2$ is not less than 1.0, preferably less than 0.2, product other than partially crystalline Beta, e.g. ZSM-5 and ZSM-12 will result. The reaction mixture $SiO_2/Al_2O_3$ molar ratio may be from 20 to 1000, is preferably 30 to 500, and even more preferably greater than about 200. The reaction mixture for use herein differs from that required for synthesis of fully crystalline zeolite Beta according to U.S. Pat. No. 3,308,069.

DETAILED DESCRIPTION

Fully crystalline zeolites synthesized under conventional procedures have catalytic properties, but the range of product silica/alumina mole ratios for such zeolites is relatively limited. When the partly crystalline zeolites are synthesized in accordance with the present method, they exhibit silica/alumina mole ratios over a wide and higher range. They show significantly enhanced catalytic activity for certain conversions, including hydroisomerization and hydrocracking. The present method allows the reaction mixture of silica, alumina and tetraethylammonium directing agent to produce the desired partially crystalline zeolite. With these reaction mixtures, the $OH^-/SiO_2$ and $M/SiO_2$ mole ratios are critical, since an optimum $OH^-/SiO_2$ is required and $M/SiO_2$ must be less than 1.0, preferably less than 0.2.

The partly crystalline composition prepared by this method functions as well as fully crystalline zeolites, resulting in a cost savings in catalyst manufacture. The partly crystalline materials of the present invention need no binder for certain applications, such as, for example, use as catalyst in hydroisomerization.

The reaction mixture composition for the synthesis of partially crystalline zeolite Beta and other zeolites can be prepared utilizing materials which can supply the appropriate oxide. Such compositions include aluminates, alumina, silicates, silica hydrosol, silica gel, silicic acid and hydroxides. Each oxide component utilized in the reaction mixture for preparing the zeolite can be supplied by one or more essential reactants and they can be mixed together in any order. For example, any oxide can be supplied by an aqueous solution, sodium hydroxide or by an aqueous solution of a suitable silicate; the organic cation can be supplied by the directing agent compound of that cation, such as, for example, the hydroxide or a salt, e.g. halide, such as chloride, iodide or bromide. The reaction mixture can be prepared either batchwise or continuously. Crystal size and crystallization time will vary with the nature of the reaction mixture employed.

The organic directing agent source for the present method is a tetraethylammonium compound or mixtures thereof. The compound may be, as non-limiting examples, the hydroxide or the halide, e.g. bromide. The most preferred directing agent is tetraethylammonium hydroxide.

The zeolite Beta composition as prepared hereby can be identified, in terms of mole ratios of oxides and in the anhydrous state, as follows:

$$(0.1 \text{ to } 4)R_2O:(0.05 \text{ to } 2)M_{2/n}O:(0.1 \text{ to } 5)Al_2O_3:(100)SiO_2$$

wherein M is the alkali metal cation and R is the tetraethylammonium cation.

The original cations can be replaced, at least in part, by calcination and/or ion exchange with another cation. Thus, the original cations are exchanged into a hydrogen or hydrogen ion precursor form or a form in which the original cation has been replaced by a metal of Groups IIA, IIIA, IVA, IB, IIB, IIIB, IVB, VIB or VIII of the Periodic Table. Thus, for example, it is contemplated to exchange the original cations with ammonium ions or with hydronium ions. Catalytically active forms of these would include, in particular, hydrogen, rare earth metals, aluminum, metals of Groups II and VIII of the Periodic Table and manganese.

Various X-ray diffraction patterns of crystalline silicate identified as zeolite Beta are shown in U.S. Pat. No. 3,308,069, to which reference is made for details of the patterns. It is indicated in U.S. Pat. No. 3,308,069 that the appearance and disappearance of certain X-ray lines can be attributed to compositional differences in silicon to aluminum ratios in the sodium form compositions summarized in Table 2 of the patent with interplanar d-spacing (Angstroms) given in terms of intensity for several dried samples of Beta. Table 3 of U.S. Pat. No. 3,308,069 shows X-ray diffraction lines for Beta with certain variations in intensities and line appearance attributed to cation exchange of Beta. The more significant interplanar d-spacing values for exchanged Beta appear in Table 4 of U.S. Pat. No. 3,308,069.

The partially crystalline Beta prepared the present method has the characteristic X-ray diffraction shown in Table A.

TABLE A

| Interplanar d-Spacing (A) | Relative Intensity ($I/I_o$) |
|---|---|
| 11.5 ± 0.3 | M-S |
| 7.4 ± 0.2 | W |
| 6.6 ± 0.15 | W |
| 4.15 ± 0.1 | W |
| 3.97 ± 0.1 | VS |
| 3.00 ± 0.07 | W |
| 2.05 ± 0.05 | W |

These values were determined by standard technique. The radiation was the K-alpha doublet of copper, and a diffractometer equipped with a scintillation counter and a strip chart pen recorder was used. The peak heights, I, and the positions as a function of two times theta, where theta is the Bragg angle, were read from the spectrometer chart. From these, the relative intensities, 100 $I/I_o$ where $I_o$ is the intensity of the strongest line or peak, and d (obs.), the interplanar spacing in Angstrom units (A) corresponding to the recorded lines, were calculated. In Table A the relative intensities are given in terms of the symbols W=weak, M=medium, S=strong and VS=very strong. Ion exchanged forms of the zeolite manifest substantially the same pattern with some minor shifts in interplanar spacing and variation in relative intensity. Other minor variations can occur depending on the silicon to aluminum ratio of the particular sample and its thermal history.

While the improved partially crystalline composition of the present invention may be used in a wide variety of organic compound, e.g. hydrocarbon compound, conversion reactions, it is notably useful in the processes of dewaxing, hydroisomerization and cracking. Other conversion processes for which partially crystalline zeolite Beta may be utilized in one or more of its active forms include, for example, hydrocracking and converting light aliphatics to aromatics such as in U.S. Pat. No. 3,760,024.

Synthetic partly crystalline zeolite Beta prepared by the perfect method can be used either in the organic nitrogen-containing and alkali metal contaning form, the alkali metal form and hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the partially crystalline zeolite Beta such as, for example, by, in the case of platinum, treating the zeolite with a platinum metal-containing ion. Suitable platinum compounds for this purpose include chloroplatinic acid, platinous chloride and various compounds containing the platinum amine complex. Combinations of metals and methods for their introduction can also be used.

Synthetic crystalline, zeolite Beta, when employed either as an adsorbent or as a catalyst in a hydrocarbon conversion process, should be dehydrated at least partially. This can be done by heating to a temperature in the range of from about 200° C. to about 600° C. in an inert atmosphere, such as air, nitrogen, etc. and at atmospheric or subatmospheric pressures for from about 1 to about 48 hours. Dehydration can also be performed at lower temperature merely by placing the zeolite in a vacuum, but a longer time is required to obtain a particular degree of dehydration. A thermal decomposition product of this material can be created by heating same at a temperature of up to about 600° C. in an inert atmosphere for from about 1 hour to about 48 hours.

As above mentioned, the synthetic partially crystalline zeolite Beta prepared by the present method can have the original cations associated therewith replaced by a wide variety of other cations according to techniques well known in the art. Typical replacing cations include hydrogen, ammonium and metal cations including mixtures thereof. Of the replacing metallic cations, particular preference is given to cations of metals such as rare earths, Mn, Ca, Mg, Zn, Cd, Pd, Ni, Cu, Ti, Al, Sn, Fe and Co.

Typical ion exchange technique would be to contact the synthetic zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 65° C. to about 315° C. and thereafter may be calcined in air or other inert gas at temperatures ranging from about 200° C. to about 600° C. for periods of time ranging from about 1 to about 48 hours or more to produce a catalytically-active thermal decomposition product thereof.

Regardless of the cation replacing the alkali metal in the synthesized form of the partially crystalline zeolite Beta, the spatial arrangement of the aluminum, silicon and oxygen atoms which form the basic crystal lattices of the crystalline portion of the composition remains essentially unchanged by the described replacement of alkali metal as determined by taking an X-ray powder diffraction pattern of the ion-exchanged material.

Catalysts comprising the partially crystalline zeolite composition may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the partially crystalline material can be extruded before drying or dried or partially dried and then extruded.

Although not necessary for most applications, when it is desired to incorporate the partially crystalline zeolite Beta with another material, active and inactive materials and synthetic or naturally occurring zeolites as well as incorganic materials such as clays, silica and/or metal oxides, e.g. alumina, may be used. The latter may be either naturally occurring or in the form of gelatinous precipitates, sols or gels including mixtures of silica and metal oxides. Use of a material in conjunction with the partially crystalline zeolite Beta, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. Likewise, the partially crystalline composition of the present invention may be so incorporated.

Naturally occurring clays which can be composited with the hereby synthesized partially crystalline zeolite Beta include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the partially crystalline zeolite Beta can be composited, if desired, with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided partially crystalline zeolite Beta and inorganic oxide gel matrix vary widely with the zeolite Beta content ranging from about 1 to about 90 percent by weight, and more usually in the range of about 2 to about 65 percent by weight of the composite.

Employing a catalytically active form of the partially crystalline composition of this invention containing a hydrogenation component, reforming stocks can be reformed employing a temperature between 370° C. and 540° C. The pressure can be between 100 and 1000 psig, but is preferably between 200 and 700 psig. The liquid hourly space velocity is generally between 0.1 and 10 hr$^{-1}$, preferably between 0.5 and 4 hr$^{-1}$ and the hydrogen to hydrocarbon mole ratio is generally between 1 and 20, preferably between 4 and 12.

The catalyst can also be used for hydroisomerization of normal paraffins, when provided with a hydrogenation component, e.g. platinum. Hydroisomerization is carried out at a temperature between 90° C. to 370° C., preferably 140° C. to 290° C., with a liquid hourly space velocity between 0.01 and 10 hr$^{-1}$, preferably between 1 and 5 hr$^{-1}$, employing hydrogen such that the hydrogen to hydrocarbon mole ratio is between 1 and 10. Additionally, the catalyst can be used for olefin or aromatics isomerization employing temperatures between 0° C. and 370° C.

The catalyst can also be used for reducing the pour point of gas oils. This process is carried out at a liquid hourly space velocity between about 0.1 and about 10 hr$^{-1}$, a temperature between about 250° C. and about 540° C., and a pressure of between about 100 psig and about 2000 psig.

Other reactions which can be accomplished employing the catalyst of this invention containing a noble metal, e.g. platinum, or a non-noble metal, e.g. nickel, tungsten, molybdenum, cobalt and combinations thereof, include hydrocracking, hydrogenation-dehydrogenation reactions and desulfurization reactions, olefin polymerization (oligomerization), and other organic compound conversions such as the conversion of alcohols (e.g. methanol) to hydrocarbons.

In order to more fully illustrate the nature of the invention and the manner of practicing same, the following examples are presented. In the examples, product crystallinity is expressed as the ratio of the intensity of the reflection at two theta=22.5° to that of a standard sample of crystalline zeolite Beta.

EXAMPLE 1

A 0.22 gram quantity of NaAlO$_2$ and 1.16 grams NaCl were dissolved in 36.7 grams deionized water. The resulting solution was mixed with 36.9 grams tetraethylammonium bromide. To this mixture was added 51.0 ml of 3.42 N tetraethylammonium hydroxide, with agitation. This solution was transferred to a 300 ml stainless steel autoclave. Twenty-one grams of commercial silica gel was then added to the solution and stirred vigorously in the autoclave for 2 minutes. The autoclave was then sealed and heated to 160° C., stirring at 400 rpm at autogenous pressure. The reaction mixture had the composition, in mole ratios, as follows:

| | |
|---|---|
| SiO$_2$/Al$_2$O$_3$ | 400 |
| H$_2$O/SiO$_2$ | 10 |
| OH$^-$/SiO$_2$ | 0.50 |
| Na$^+$/SiO$_2$ | 0.10 |
| TEA$^+$/SiO$_2$ | 1.0 |

The reaction was terminated at 3 days and the solid product was filtered from the reaction liquid, washed with water, and dried at about 110° C.

The solid product was submitted for chemical analysis and X-ray diffraction analysis. Analytical composition of the solid product, in weight percent, proved to be:

| | |
|---|---|
| SiO$_2$ = | 81.6 |
| Al$_2$O$_3$ = | 0.35 |
| Na = | not detected |
| C = | 8.52 |
| N = | 1.29 |
| Ash = | 74.0 |
| SiO$_2$/Al$_2$O$_3$ mole ratio = | 396. |

X-ray analysis proved the product to be 50% crystalline zeolite Beta having characteristic lines set forth in Table A.

EXAMPLE 2

A 0.22 gram quantity of NaAlO$_2$, 1.9 grams of NaCl, and 36.9 grams of tetraethylammonium bromide were dissolved in 40.1 grams of deionized water. To this solution was added 47.6 ml of 3.66 N tetraethylammonium hydroxide. The resulting solution was added to 21.0 grams of commercial silica gel in a 300 ml stainless steel autoclave. The mixture, having the same composition as in Example 1, was stirred for 30 seconds, then the autoclave was sealed and stirring and heating begun.

This reaction mixture was heated at 160° C. with stirring (400 rpm) for 65 hours before the autoclave was quenched in an ice bath to terminate crystallization.

The final solid product was processed as in Example 1. X-ray analysis of the product showed the material to be 0% crystalline zeolite Beta. The analytical SiO$_2$/Al$_2$O$_3$ ratio of the product was found to be 212.

EXAMPLE 3

A 0.22 gram quantity of NaAlO$_2$, 1.2 grams of NaCl, and 36.9 grams of tetraethylammonium bromide were dissolved in 36.7 grams of deionized water. To this solution was added 51.0 ml of 3.44 N tetraethylammonium hydroxide. The resulting solution was mixed with 21.0 grams of HiSil silica gel (precipitated hydrated SiO$_2$ containing about 6 weight percent free H$_2$O and 4.5 weight percent bound H$_2$O of hydration and having a particle size of about 0.02 micron). The solution was then allowed to stand at room temperature for 5 days. The reaction mixture had the same composition in mole ratios as that of Example 1, except that the value of the ratio TEA$^+$/SiO$_2$ was 0.1

After the digestion period the hydrogel was transferred to a 300 ml stainless steel autoclave and reacted with stirring (400 rpm) at 160° C. The crystallization was terminated at 5 days.

The final product was processed as in Example 1. X-ray analysis of the product showed the material to be 90% crystalline zeolite Beta. By chemical analysis the Beta product was found to have a SiO$_2$/Al$_2$O$_3$ molar ratio of 156.

EXAMPLE 4

A 0.3 gram quantity of NaAlO$_2$ was dissolved in 21.1 grams of deionized water. To this solution was added 100.3 ml of 3.48 N tetraethylammonium hydroxide. The resulting solution was added to 21.0 grams of commercial silica$_2$ gel in a 300 ml stainless steel autoclave as described in Example 2. The hydrogel was reacted at 160° C. with stirring at 400 rpm. The reaction was permitted to proceed for 2 days.

X-ray analysis of the final product showed the material to be 70% crystalline zeolite Beta. The chemical SiO$_2$/Al$_2$O$_3$ molar ratio of this product was found to be 140.

EXAMPLE 5

A 0.32 gram quantity of NaAlO$_2$ and 1.26 grams of NaCl were dissolved in 41.2 grams of deionized water. To this solution was added 130.2 ml of 3.45 N tetraethylammonium hydroxide. The resulting solution was added to 104.2 grams of tetraethylorthosilicate in a 300 ml stainless steel autoclave. The mixture, having a composition, in mole ratios, as follows:

| | |
|---|---|
| SiO$_2$/Al$_2$O$_3$ | 400 |
| H$_2$O/SiO$_2$ | 10 |
| OH$^-$/SiO$_2$ | 0.90 |
| Na$^+$/SiO$_2$ | 0.05 |
| TEA$^+$/SiO$_2$ | 0.90, | was reacted at 160° C. with stirring at 400 rpm. Reaction was permitted to proceed for 24 hours.

X-ray analysis of this product proved it to be 90% crystalline zeolite Beta. By chemical analysis, this zeolite Beta product was found to have a SiO$_2$/Al$_2$O$_3$ molar ratio of 106.

EXAMPLE 6

A 1.5 gram quantity of NaAlO$_2$ was dissolved in 63.0 grams of deionized water. A second solution was produced by dissolving 15.6 grams of tetraethylammonium bromide in 60.2 ml of 3.42 N tetraethylammonium hydroxide. then mixing it with the fist solution. The resulting solution was then added to 21.0 grams of HiSil silica gel in a 300 ml stainless steel autoclave.

The reaction mixture had the composition, in mole ratios:

| | |
|---|---|
| SiO$_2$/Al$_2$O$_3$ | 60 |
| H$_2$O/SiO$_2$ | 15 |
| OH$^-$/SiO$_2$ | 0.60 |
| Na$^+$/SiO$_2$ | 0.05 |
| TEA$^+$/SiO$_2$ | 0.80 |

The autoclave was immediately sealed and stirring, and heating, begun. The hydrogel was reacted at 160° C. with stirring at 400 rpm. Reaction was terminated after 2 days.

X-ray analysis of the product showed the material to be 70% crystalline zeolite Beta. The SiO$_2$/Al$_2$O$_3$ molar ratio of this product was found to be 43.

EXAMPLE 7

To show utility of the new zeolite Beta composition, it was tested for hydroisomerization of hexadecane. Three separate catalysts were tested to provide comparison. The first catalyst was a fully crystalline zeolite Beta synthesized in accordance with U.S. Pat. No. 3,308,069 and having a silica/alumina mole ratio of 30. The second catalyst was the dealuminized product of the fully crystalline first catalyst. Dealumination was conducted by the method of European Patent Application 95,304, incorporated herein by reference as to that method.

The third catalyst was the product of Example 1, a partially crystalline zeolite Beta composition of the present invention.

Prior to testing, each catalyst was exchanged to the ammonium form with 1M NH$_4$Cl solution at 90° C. reflux for an hour followed by platinum (0.6 wt. %) exchange of the tetrammine complex at room temperature overnight. The platinum-exchanged material was thoroughly washed, oven dried at 130° C. and air calcined at 350° C.

The catalysts were then placed, in turn, in a reactor and contacted with hexadecane in the presence of hydrogen. The test temperature was maintained at 250°-350° C., the pressure at 500 psig, and the liquid hourly space velocity at 1 hr$^{-1}$. Product Iso-C$_{16}$ and conversion percentages were measured over the test. From the results presented in Table B, it is observed that the partially crystalline zeolite Beta composition performed essentially as effectively as the much more expensive dealuminized fully crystalline zeolite Beta, and significantly better than the fully crystalline Beta having a silica/alumina mole ratio of 30.

TABLE B

| Iso-C$_{16}$ at | First Catalyst- 30/1 Beta | Second Catalyst- Dealuminized Beta | Third Catalyst- Partially Crystalline Beta |
|---|---|---|---|
| 40% Conversion | 39 | 40 | 40 |
| 60% Conversion | 50 | 60 | 57 |
| 80% Conversion | 59 | 78 | 72 |

What is claimed is:

1. A method for synthesizing a large pore size synthetic zeolite by (i) preparing a mixture comprising sources of alkali metal cations, an oxide of aluminum, organic cations, an oxide of silicon and water, (ii) maintaining the mixture under crystallization conditions, (iii) terminating the crystallization when the zeolite product is from 30% to 90% crystalline by X-ray analysis, and (iv) recovering the partly crystalline product containing alkali metal cations and having a higher silica:alumina ratio than the fully crystalline product and being from 30% to 90% crystalline.

2. A method for synthesizing highly siliceous zeolite Beta which comprises (i) preparing a mixture capable of forming said zeolite Beta, said mixture comprising sources of alkali metal cations (M), an oxide of aluminum, tetraethylammonium cations (R), an oxide of silicon and water and having a composition, in terms of mole ratios, within the following ranges:

| | |
|---|---|
| SiO$_2$/Al$_2$O$_3$ | 20–1000 |
| H$_2$O/SiO$_2$ | 5–200 |
| OH$^-$/SiO$_2$ | 0.10–2.0 |
| M/SiO$_2$ | 0.01–1.0 |
| R/SiO$_2$ | 0.10–2.0 |

(ii) maintaining the mixture at a temperature of from about 90° C. to about 200° C. for crystallization of said zeolite Beta, (iii) terminating crystallization when said zeolite Beta is from about 30% to about 90% crystalline by X-ray analysis, and (iv) recovering zeolite Beta containing alkali metal cations and being from about 30% to about 90% crystalline by X-ray analysis and having a composition in terms of more ratios of oxides in the anhydrous state of:

(0.1 to 4)R$_2$O:(0.05 to 2)M$_{2/n}$O:(0.1 to 5)Al$_2$O$_3$:(100)SiO$_2$.

3. The method of claim 2 wherein said mixture has a composition, in terms of mole ratios, as follows:

| | |
|---|---|
| $SiO_2/Al_2O_3$ | 30–500 |
| $H_2O/SiO_2$ | 10–100 |
| $OH^-/SiO_2$ | 0.2–1.0 |
| $M/SiO_2$ | 0.05–0.20 |
| $R/SiO_2$ | 0.20–1.0 |

4. The method of claim 2 which comprises the further step of calcining said zeolite Beta recovered in step (iv) at a temperature of from about 200° C. to about 600° C.

5. The method of claim 3 which comprises the further step of calcining said zeolite Beta recovered in step (iv) at a temperature of from about 200° C. to about 600° C.

6. The method of claim 4 comprising replacing alkali metal cations of the calcined zeolite Beta, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements.

7. The method of claim 5 comprising replacing alkali metal cations of the calcined zeolite Beta, at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB and VIII of the Periodic Table of Elements 8. The method of claim 6 wherein said replacing cation is hydrogen or a hydrogen precursor.

9. The method of claim 7 wherein said replacing cation is hydrogen or a hydrogen precursor.

10. The method of claim 8 which comprises the further step of heating the product zeolite Beta from the alkali metal cation replacing step at a temperature of from about 200° C. to about 600° C.

11. The method of claim 9 which comprises the further step of heating the product zeolite Beta from the alkali metal cation replacing step at a temperature of from about 200° C. to about 600° C.

* * * * *